US012788305B2

(12) United States Patent
Shtober

(10) Patent No.: US 12,788,305 B2
(45) Date of Patent: Nov. 10, 2026

(54) SYSTEM AND METHOD FOR SECONDARY BRAIN INSULT DETECTION

(71) Applicant: Gad Matania Shtober, Jerusalem (IL)

(72) Inventor: Gad Matania Shtober, Jerusalem (IL)

( * ) Notice: Subject to any disclaimer, the term of this patent is extended or adjusted under 35 U.S.C. 154(b) by 577 days.

(21) Appl. No.: 18/023,729

(22) PCT Filed: Aug. 31, 2021

(86) PCT No.: PCT/IL2021/051067
§ 371 (c)(1),
(2) Date: Feb. 28, 2023

(87) PCT Pub. No.: WO2022/049575
PCT Pub. Date: Mar. 10, 2022

(65) Prior Publication Data

US 2023/0309903 A1 Oct. 5, 2023

Related U.S. Application Data

(60) Provisional application No. 63/073,935, filed on Sep. 3, 2020.

(51) Int. Cl.
*A61B 5/00* (2006.01)
*A61B 5/145* (2006.01)
*A61B 5/1459* (2006.01)

(52) U.S. Cl.
CPC .......... *A61B 5/4064* (2013.01); *A61B 5/0086* (2013.01); *A61B 5/14532* (2013.01);
(Continued)

(58) Field of Classification Search
CPC . A61B 5/4064; A61B 5/0086; A61B 5/14532; A61B 5/14546; A61B 5/1459;
(Continued)

(56) References Cited

U.S. PATENT DOCUMENTS

2006/0234386 A1 10/2006 Burns
2008/0139908 A1 6/2008 Kurth
(Continued)

FOREIGN PATENT DOCUMENTS

CN 102014746 4/2011

OTHER PUBLICATIONS

Sakudo, Akikazu, "Near-infrared spectroscopy for medical applications: Current status and future perspectives" Clinica Chimica Acta, 455 (2016): 181-188, Feb. 12, 2016 (Feb. 12, 2016).
(Continued)

*Primary Examiner* — Jeffrey G. Hoekstra
(74) *Attorney, Agent, or Firm* — JMB DAVIS BEN-DAVID

(57) ABSTRACT

Disclosed herein is a system comprising at least one probe configured for obtaining from a brain tissue at least one near infrared measurement when the at least one probe is positioned at a predetermined proximal location to brain tissue, a processor configured to receive the at least one near infrared measurement from the at least one probe, compare the at least one near infrared measurement with a predetermined threshold value for at least one predetermined compound, determine the at least one near infrared measurement is above the predetermined threshold value, generate an indication indicating the presence of a secondary brain insult in the brain tissue, and provide the indication to an output thereby notifying an operator of the at least one probe of the presence of the secondary brain insult in the brain tissue.

11 Claims, 7 Drawing Sheets

(52) U.S. Cl.
CPC ........ *A61B 5/14546* (2013.01); *A61B 5/1459* (2013.01); *A61B 5/742* (2013.01); *A61B 2560/0223* (2013.01)

(58) Field of Classification Search
CPC ........... A61B 5/742; A61B 2560/0223; A61B 5/4088; A61B 5/7282; A61B 5/1455; A61B 5/14553; A61B 5/0075; A61B 5/6868
See application file for complete search history.

(56) References Cited

U.S. PATENT DOCUMENTS

| | | | |
|---|---|---|---|
| 2010/0268096 | A1 | 10/2010 | Berka |
| 2014/0002075 | A1 | 1/2014 | Lin |
| 2015/0103360 | A1 | 4/2015 | Addison |
| 2015/0150453 | A1 | 6/2015 | Abreu |
| 2019/0159675 | A1 | 5/2019 | Sengupta |

OTHER PUBLICATIONS

Seule Martin et al, "Evaluation of a New Brain Tissue Probe for Intracranial Pressure, Temperature, and Cerebral Blood Flow Monitoring in Patients with Aneurysmal Subarachnoid Hemorrhage", Neurocritical Care, Springer US, New York, vol. 25, No. 2, Jun. 1, 2016 (Jun. 1, 2016), pp. 193-200.

Smith et al, "Neuromonitoring", Anaesthesia, Elsevier, Amsterdam, NL, vol. 9, No. 5, May 1, 2008 (May 1, 2008), pp. 187-192.

Griffiths Heidi et al, "Brain Metabolism and Severe Pediatric Traumatic Brain Injury", Child's Nervous System, Springer, Berlin, DE, vol. 33, No. 10, Sep. 6, 2017 (Sep. 6, 2017), pp. 1719-1726.

SYSTEM AND METHOD FOR SECONDARY BRAIN INSULT DETECTION

CROSS-REFERENCE TO RELATED APPLICATIONS

This is the U.S. National Stage of International Patent Application No. PCT/IL2021/051067, filed Aug. 31, 2021, which in turn claims the benefit of U.S. Provisional Patent Application No. 63/073,935, filed on Sep. 3, 2020.

FIELD

The invention relates to the field of brain insult detection.

BACKGROUND

Traumatic brain injury or insult is defined as a major insult to the nerves and the nerve supporting tissues in the brain. Two types of brain injuries can occur, a primary or major brain insult and a secondary insult. The major traumatic brain injury is generally characterized with tearing and physical insult caused to the brain tissue. The secondary brain insult is generally characterized by a biomechanical cascading resulting from the effects of the primary insult to the brain tissue. The biochemical cascade produces excitotoxicity agents such as Glutamate. The excitotoxicity affects the cell biochemistry and therefore changes Glucose, Lactate and Pyruvate levels and cause differences in osmotic pressure on the brain.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided in accordance with an embodiment a system comprising one or more probes configured for obtaining from a brain tissue on one or more near infrared measurements when the at least one probe positioned at a predetermined proximal location to brain tissue.

A processor configured to receive the at least one near infrared measurements from the one or more probes; compare the one or more near infrared measurements with a predetermined threshold value for one or more predetermined compounds, determine the one or more near infrared measurements is above the predetermined threshold value, generate an indication indicating the presence of a secondary brain insult in the brain tissue, and provide the indication to an output thereby notifying an operator of the one or more probes of the presence of the secondary brain insult in the brain tissue.

In certain embodiments, a first probe of the one or more probes is positioned adjacent to a primary insult and a second probe of the one or more probes is positioned adjacent to the medulla oblaganta of a subject and other positions on the scull In certain embodiments, the probe includes at least one camera operative to provide a visual feedback of the location of the probe within the brain tissue.

In certain embodiments, the output includes a display operative to display the indication as a color.

In certain embodiments, the probe includes an emitter operative to emit near infrared light in a direction of the brain tissue, a detector operative to measure the near infrared measurement from a reflected light reflected from the brain tissue.

In certain embodiments, the probe includes a first fiber bundle configured to direct the near infrared light from the emitter to the brain tissue, and a second fiber bundle configured to direct the reflected light from the brain tissue to the detector.

In certain embodiments, the system further includes a memory unit configured to store the predetermined threshold value, store the near infrared measurement, and store a location where the secondary brain insult is detected.

In certain embodiments, the processor is configured to operate the probe to obtain the infrared measurements.

In certain embodiments, the probe is calibrated to collect said near infrared measurements associated with the predetermined compound.

In certain embodiments, the predetermined compound is Glutamate.

In certain embodiments, the predetermined compound is Glucose.

In certain embodiments, the predetermined compound is Lactate.

In certain embodiments, the predetermined compound is Pyruvate.

There is further provided in accordance with an embodiment a method for detecting a secondary brain insult, the method includes using a hardware processor for receiving an infrared measurement from a probe inserted into a brain tissue, comparing the near infrared measurement with a predetermined threshold value, determining the near infrared measurement is above the predetermined threshold value, generating an indication indicating the presence of the secondary brain insult in the brain tissue, and providing the indication to an output thereby notifying an operator of the probe of the presence of the secondary brain insult.

In certain embodiments, the method further includes using the hardware processor for storing the near infrared measurement and the location of the secondary brain insult a memory unit.

In certain embodiments, the near infrared measurement is compared to a predetermined threshold value indicating a high concentration of Glutamate in the brain tissue.

In certain embodiments, the near infrared measurement is compared to a predetermined threshold value indicating a high concentration of Glucose in the brain tissue.

In certain embodiments, the near infrared measurement is compared to a predetermined threshold value indicating a high concentration of Lactate in the brain tissue.

In certain embodiments, the near infrared measurement is compared to a predetermined threshold value indicating a high concentration of Pyruvate in the brain tissue.

There is further provided in accordance with an embodiment a computer program product detecting a secondary brain insult, the computer program product including a non-transitory computer-readable storage medium having program code embodied therewith, the program code executable by a hardware processor to receive a near infrared measurement from a probe, compare the near infrared measurement with a predetermined threshold value, determine the near infrared measurement is above the predetermined threshold value, generate an indication indicating the presence of a secondary brain insult in the brain tissue, and provide the indication to an output to notify an operator of the probe of the presence of the secondary brain insult.

In certain embodiments, the computer program product detecting the secondary brain insult is further configured to store the near infrared measurement a location of the secondary brain insult in a memory unit.

In certain embodiments, the near infrared measurement is compared to a predetermined threshold value indicating a high concentration of Glutamate in the brain tissue.

In certain embodiments, the near infrared measurement is compared to a predetermined threshold value indicating a high concentration of Glucose in the brain tissue.

In certain embodiments, the near infrared measurement is compared to a predetermined threshold value indicating a high concentration of Lactate in the brain tissue.

In certain embodiments, the near infrared measurement is compared to a predetermined threshold value indicating a high concentration of Pyruvate in the brain tissue.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Disclosed herein is a system and method for secondary brain insult detection, according to exemplary embodiments.

Figure 1A:
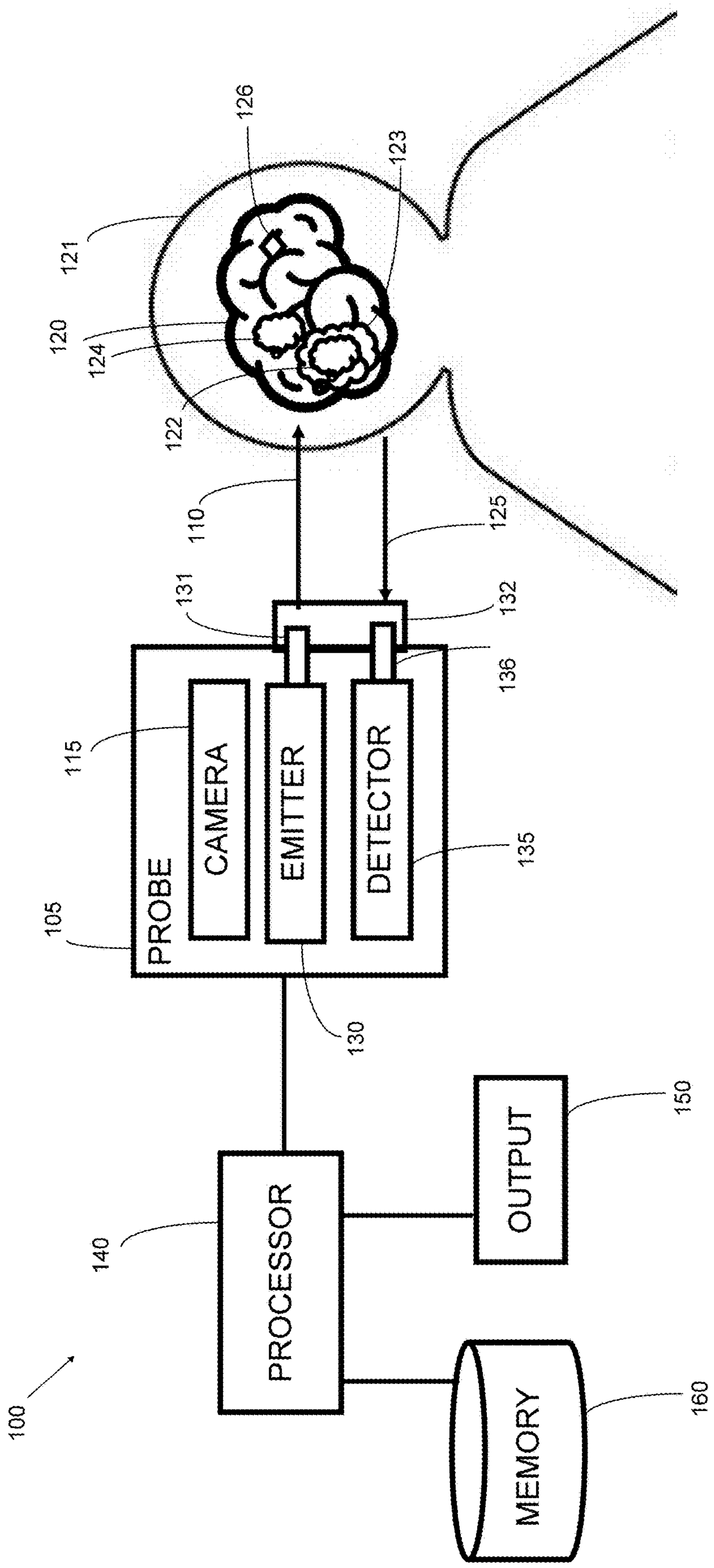
FIGS. 1A-1D schematically illustrate a system configured to detect the presence of a secondary brain insult in brain tissue, according to certain embodiments.

FIG. 1A schematically illustrates a system 100 configured for detecting the presence of a secondary brain insult 122 in a brain tissue 123 of a subject 121, according to certain embodiments. System 100 includes one or more probes, representing any number of probes, schematically illustrated as a single prove with item number 105. Probes 105 are configured to be inserted into brain 120 of a subject for collecting near infrared ("NIR") measurements that can be indicative of the presence of secondary brain insult 122. Probe 105 includes an emitter 130 configured to emit a NIR light 110, having a predetermined wavelength in the electromagnetic spectrum region between 700 to 2,500 nanometers ("nm"), for example, within the spectral range of 1650-2250 nm. This spectral range is derived to a first derivative spectra, for example, by implementing the Savitsky Gollay equation with a first derivative and smoothing every three points for a spectral range using the equation:

$$x_{i2D} = \frac{x_i}{\max(x) - \min(x)}$$

The selected spectral range is represented by x. The resulting minimum value, 0.976, and maximum value, 0.390, are not 0 and 1 respectively. The normalization of the range is then performed to find the maximum and the minimum for each spectrum that divides each point in the spectrum by the value (max-min). The net result is of the total range covered by each spectrum, which is exactly one. $X_{21D}$ represents a second derivative for each spectral point in the spectral range of 1650-2250 nm. Each wavelength is divided with the sum of a maximum absorbance, max(x), minus a minimum absorbance, min(x), of the entire spectral range. For example, 1650 nm is divided by a maximum absorbance of 2.1 minus a minimum absorbance of 0.6, providing a result of 1,100 nm.

Transmitted or reflected light, referred generally as 115, reflects from brain tissue 123 and is detected by a detector 135 of probe 105 and measured as NIR measurements. A processor 140 is configured to receive the NIR measurements from probe 105 and to analyze the NIR measurements to generate a determination whether a secondary brain insult 122 is present in brain tissue 123. In certain embodiments, probe 105 includes one or more fiber bundles 132, including a first fiber 131 configured to carry NIR light 110 from emitter 130 to brain tissue 120 and a second fiber 136 to carry light reflected 115 from brain tissue 120 to detector 135.

In certain embodiments, processor 140 can execute the analysis of the NIR measurements through NIR spectroscopy to identify biomechanical changes in brain tissue 123 by measuring the concentration of predetermined compounds in brain tissue 123 which provides an indication of the presence of secondary brain insult 122.

The NIR spectroscopy detects vibrating overtones of functional groups containing hydrogen, which have fundamental absorptions in the mid-infrared region of the spectrum. The NIR spectroscopy can be used to detect molecules having carbon-hydrogen, nitrogen-hydrogen, oxygen-hydrogen and sulfur-hydrogen bonds and/or the like, which are strong absorbers. It has been observed that secondary brain insult 122 results in biochemical changes in brain 120 resulting from increased glucose, pyruvate, lactate and Glutamate concentrations. Therefore, configuring and calibrating processor 140 to execute NIR spectroscopy to identify Glutamate, Glucose, Lactate and Pyruvate and/or the like, above a predetermined threshold value provides an indication that secondary brain insult 122 is occurring in brain tissue 123.

After analyzing the measurements, processor 140 generates an indication whether there is secondary brain insult 122 in brain tissue 123 or brain tissue 122 is clear. Processor 140 can provide the indication to an output 150, for example a display screen, a light indicator, a sound generating device and/or the like. System 100 can include a memory unit 160, configured to store information regarding the location of secondary brain insult 122, the concentrations of the compounds found in the vicinity of secondary brain insult 122, the NIR measurement, the predetermined threshold values of the compounds Glutamate, Glucose, Lactate and Pyruvate and/or the like.

Figure 1B:
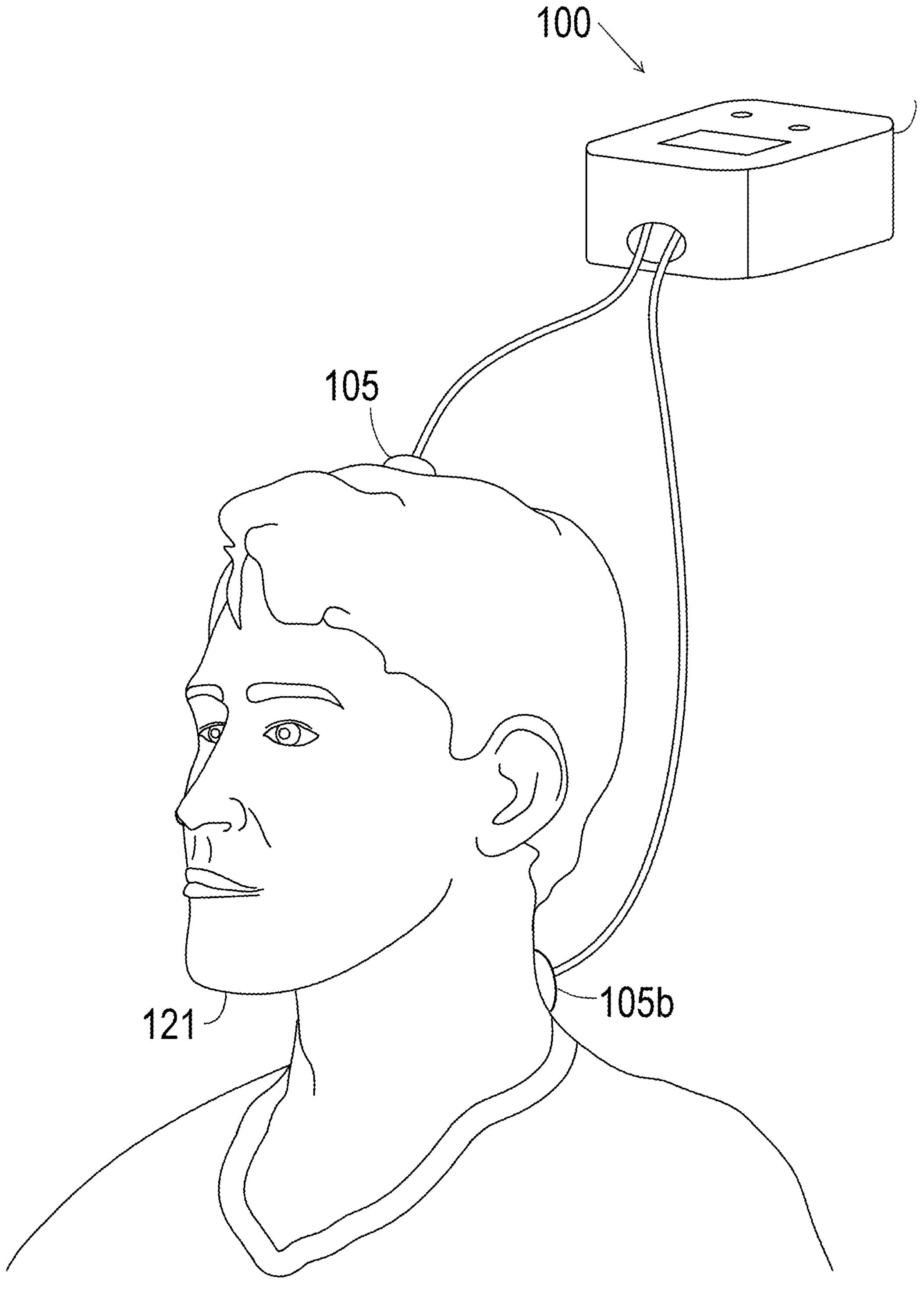

FIG. 1B schematically illustrates system 100 having a first probe 105*a* can be inserted adjacent to a primary insult 124 (FIG. 1A) in brain 120 (FIG. 1A) and a second probe 105*b* can be inserted adjacent to a medulla oblaganta (not shown). The probes 105*a*, 105*b* can be arranged on a skull (not shown) of subject 121, above dura matter inside the skull or an epidural space in an upper spinal cord, the medulla oblaganta or the like, of subject 121.

Figure 1C:
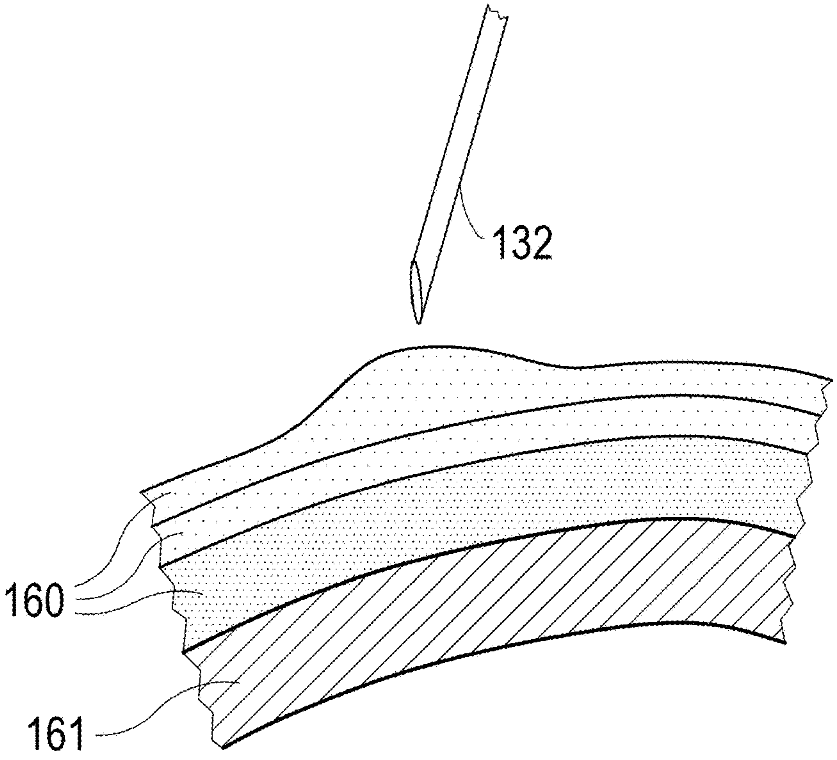
Figure 1D:
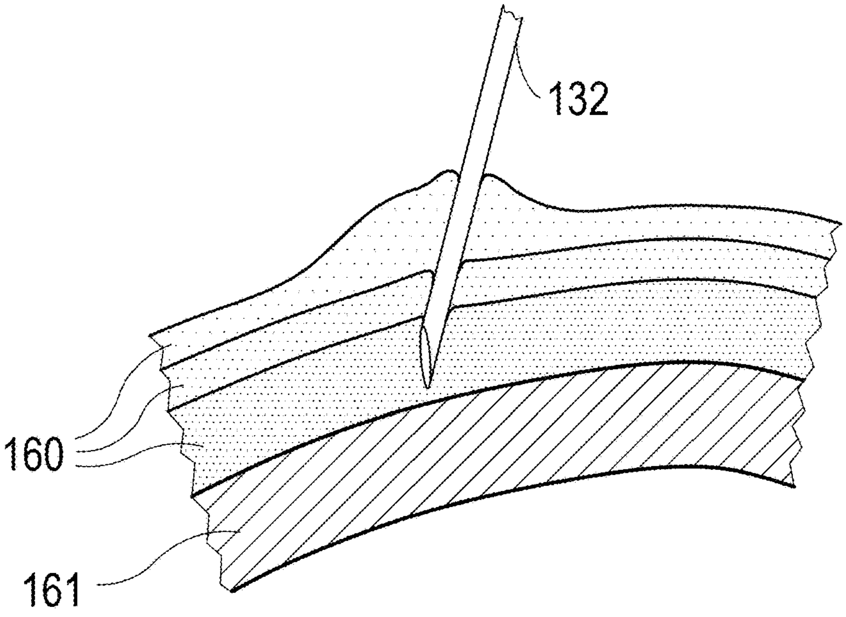

FIGS. 1C-1D schematically illustrate one or more fiber bundles inserted into subject 121 through skin and skull bone 160 to be positioned adjacent to dura matter 161, according to certain exemplary embodiments.

Figure 2:
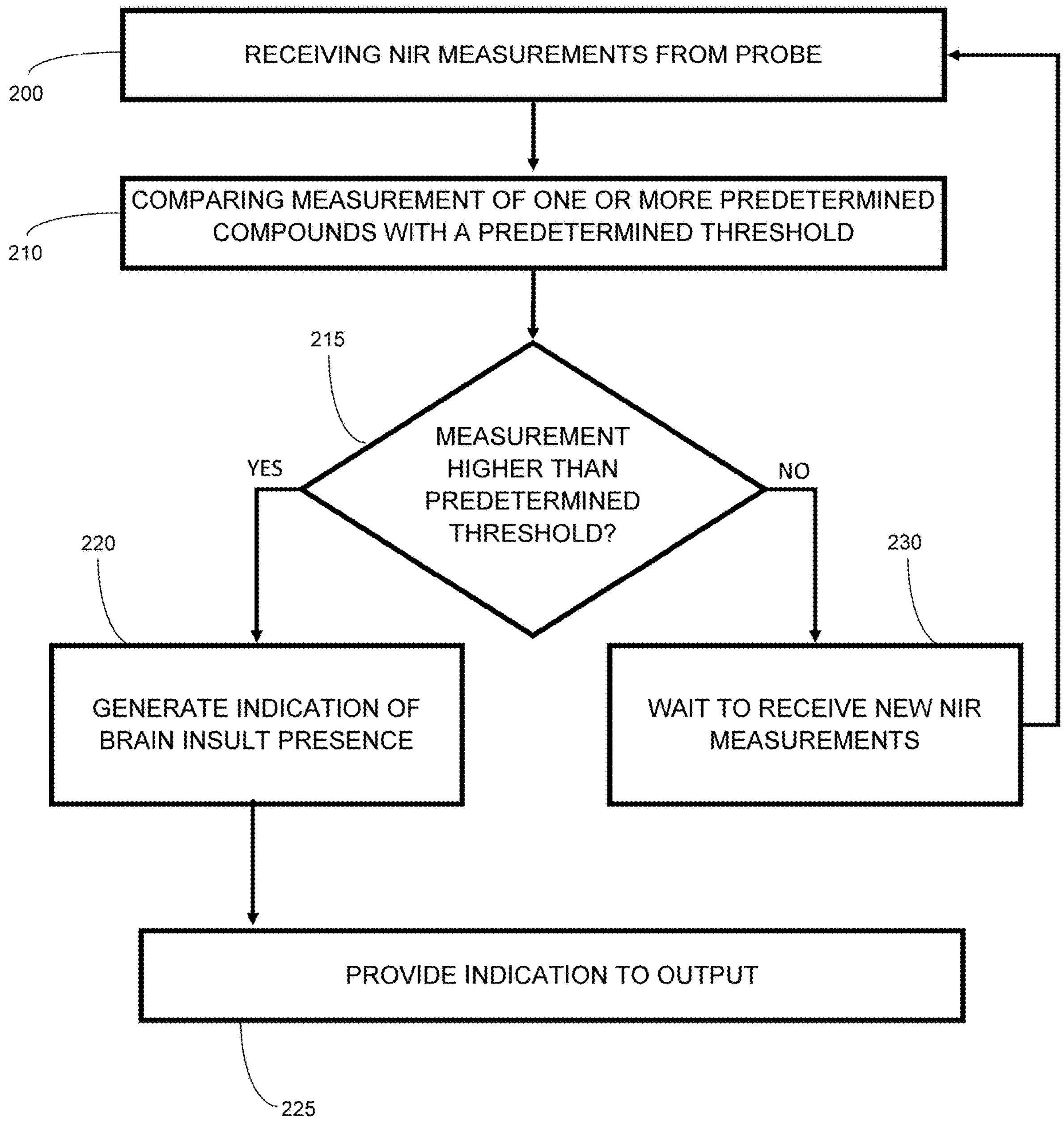
FIG. 2 shows a method of operation for detecting the second brain insult in the brain tissue, according to certain embodiments.

FIG. 2 shows a method of operation for detection of secondary brain insult 122 (FIG. 1) in brain tissue 123 (FIG. 1), according to certain embodiments. In operation 200, processor 140 (FIG. 1) obtains NIR measurements from probe 105 (FIG. 1). Processor 140 is configured to operate probe 105 to obtain NIR measurements of brain tissue 123. The NIR measurements obtained by probe 105 are received by processor 140.

In operation 210 processor 140 compares the NIR measurements with a predetermined threshold values of predetermined compounds. Processor 140 analyzes the NIR measurements and refers them to a spectral correlation to the chemical values of predetermined compounds such as Glutamate, Glucose, Lactate and Pyruvate and/or the like, thereby determining whether the quantity levels of the predetermined compounds in brain tissue 122 is indicative of secondary brain insult 122. The spectral correlation to the chemical values of predetermined compounds and the predetermined threshold values can be stored in memory unit 160.

In operation 215, processor 140 determines whether the NIR measurements are higher than a predetermined threshold value. Processor 140 determines the NIR measurements are higher than the predetermined threshold values by comparing the NIR measurements and the predetermined threshold values.

In operation 220, processor 140 generates an indication that there is a secondary brain insult 122 in brain tissue 123. Processor 140 generates the indication that will inform an operator of probe 105 that probe 105 is directed at a location of secondary brain insult 122.

In operation 225, processor 1440 provides the indication to output 150 (FIG. 1). Processor 140 provides the indication to output 150 to notify the operator of the presence of secondary brain insult 122 in brain tissue 123. Output 150 can be a display showing a message to the operator, output 150 can generate a sound or a light thereby informing the operator of the presence of secondary brain insult 122.

In operation 230, processor 140 waits for new NIR measurements when the NIR measurements are less than the predetermined threshold value. Where processor 140 generates a determination that the NIR measurements are less than the predetermined threshold value, processor 140 can generate an indication that no secondary brain insult is present in brain tissue 123, for example, providing a red light or the like. Processor 140 returns to Step 200 and waits to receive new NIR measurements from probe 105.

Figure 3:
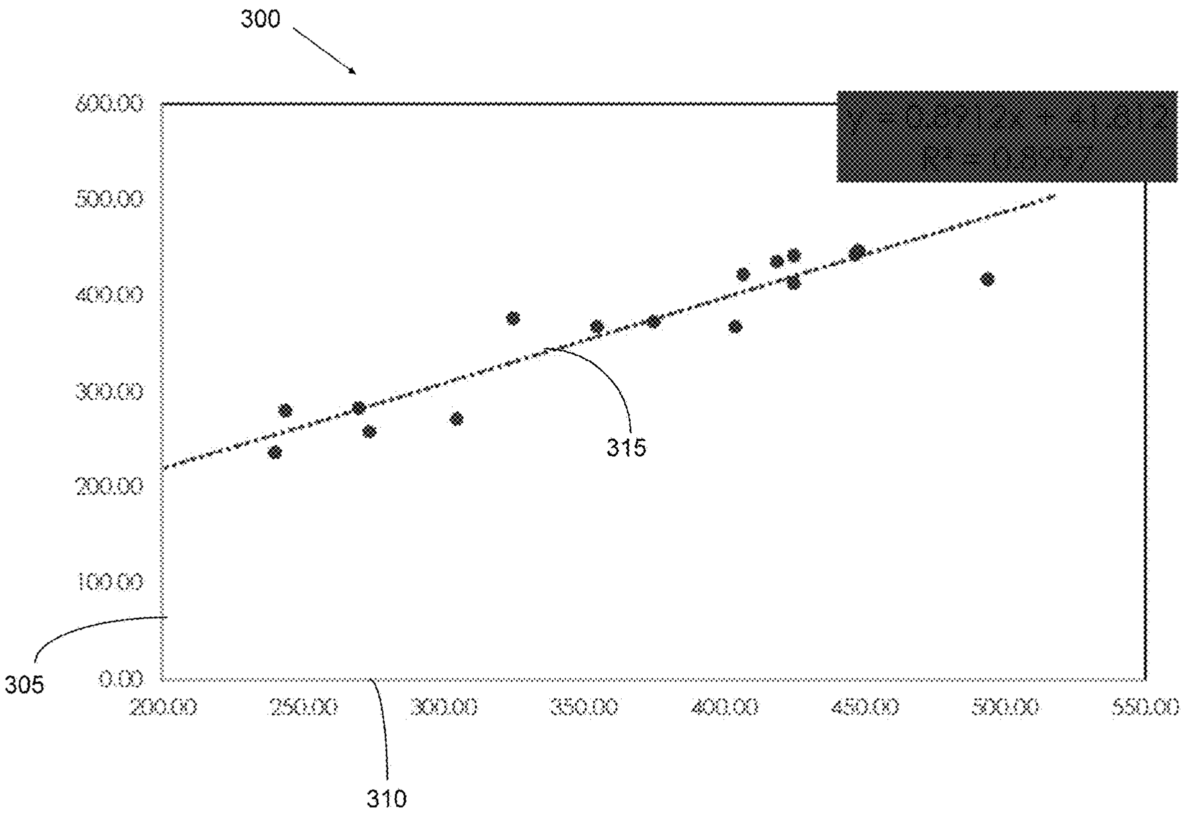
FIG. 3 illustrates a graph showing results of measuring Glutamate according to near-infrared spectroscopy by the system of FIG. 1A and through a standard chemical measurement, according to certain embodiments.

FIG. 3 shows a graph 300 showing measurements of Glutamate in brain tissue 122 (FIG. 1) during the occurrence of secondary brain insult 122 (FIG. 1), according to certain embodiments. Graph 300 includes x-axis 310 showing Glutamate concentration values obtained during an intrusive chemical method for detection of secondary brain insult. Graph 300 includes a y-axis 305 showing Glutamate concentration values predicted from NIR spectroscopy.

Figure 4:
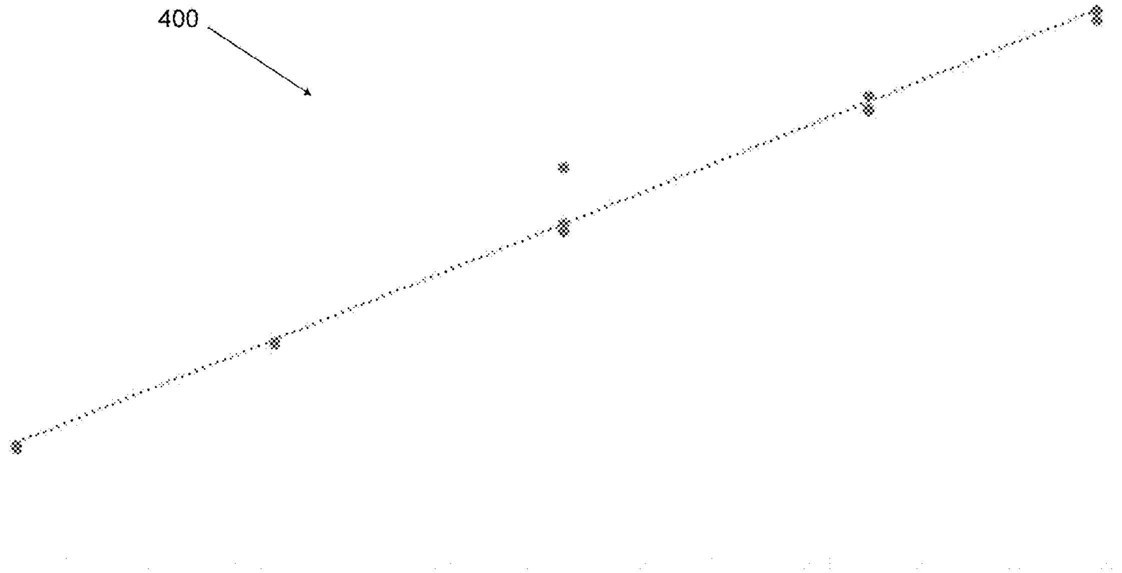
FIG. 4 illustrates a graph showing results of measuring Glucose according to near-infrared spectroscopy by the system of FIG. 1A and through a standard chemical measurement, according to certain embodiments.

FIG. 4 shows a graph 400 illustrating a correlation between the NIR measurements and the chemical measurements of Glucose levels in secondary brain insult 122 (FIG. 1), according to certain embodiments. X-axis values shows the glucose concentration values obtained through a standard intrusive chemical method. Y-axis values show the glucose concentration values predicted from using NIR spectroscopy.

Figure 5:
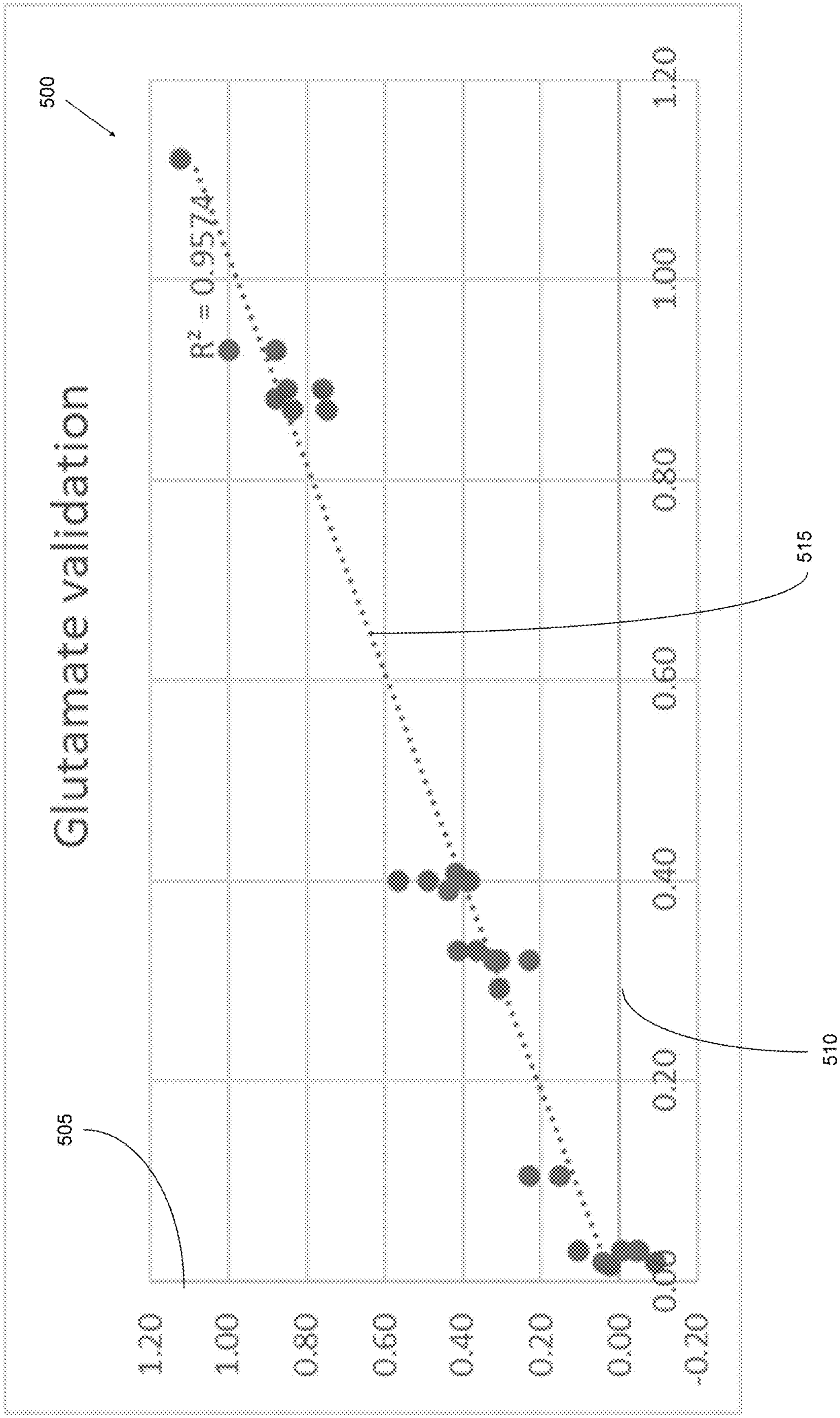
FIG. 5 shows a graph showing a second result of an experiment for obtaining Glutamate measurements through the system of FIG. 1A and the method of FIG. 2, according to certain exemplary embodiments; and, FIG. 6 shows a graph showing a second result of an experiment for obtaining Lactate measurements through the system of FIG. 1A and the method of FIG. 2, according to certain exemplary embodiments.

FIG. 5 shows a graph 500 showing a second result of an experiment for obtaining Glutamate measurements through the system of FIG. 1 and the method of FIG. 2, according to certain exemplary embodiments. Graph 500 includes an x-axis 510 providing glutamate measurement values obtained through a chemical enzyme-linked immunosorbent assay ("ELISA") method and a y-axis 505 showing glutamate measurements provided by the method disclosed herein in FIG. 2. A linear graph 515 shows a correlation between the measurements of the ELISA method and the measurements obtained via the method of FIG. 2. The correlation is high and provides evidence that the method of operation of FIG. 2 is capable identifying a glutamate percentage in brain tissue 123 (FIG. 1) with great similarity to the chemical ELISA method while being less invasive.

Figure 6:
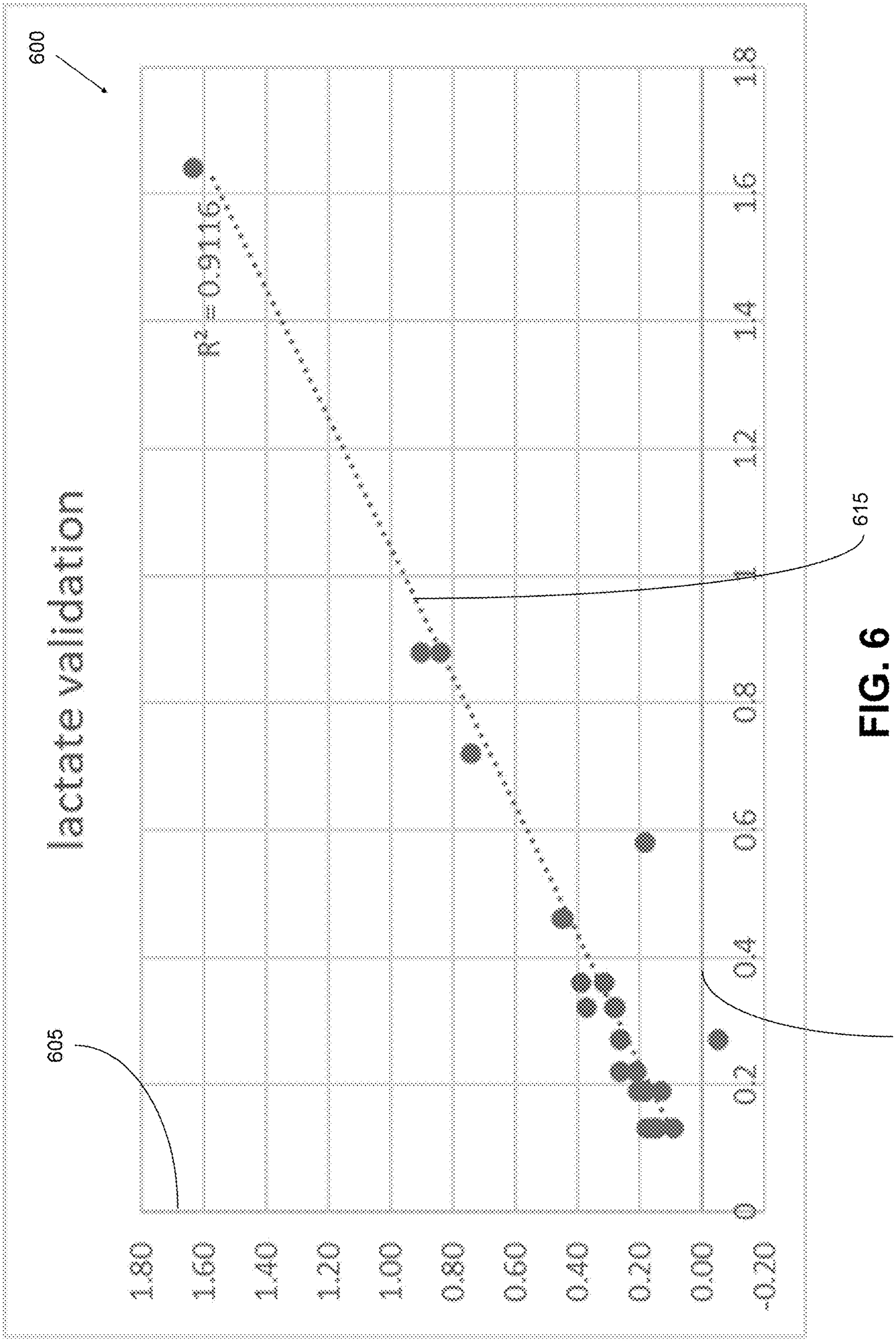

FIG. 6 shows a graph 600 showing a second result of an experiment for obtaining Lactate measurements through the system of FIG. 1 and the method of FIG. 2, according to certain exemplary embodiments. Graph 600 includes an x-axis 610 providing lactate measurement values obtained through a chemical enzyme-linked immunosorbent assay ("ELISA") method and a y-axis 505 showing lactate measurements provided by the method disclosed herein in FIG. 2. A linear graph 515 shows a correlation between the measurements of the ELISA method and the measurements obtained via the method of FIG. 2. The correlation is high and provides evidence that the method of operation of FIG. 2 is capable identifying a lactate percentage in brain tissue 123 (FIG. 1) with great similarity to the chemical ELISA method.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system for detecting second brain injury, the system comprising:

at least one probe configured for obtaining from a brain tissue at least one near infrared measurement when said at least one probe is positioned at a predetermined proximal location to brain tissue, wherein the near infrared measurement is associated with at least one predetermined compound that is an excitotoxicity agent produced due to biomechanical cascading resulting in a secondary brain insult, wherein the near infrared measurement is spectrally processed and calibrated to directly detect a concentration level of at least one predetermined excitotoxic compound elected from glutamate, lactate, pyruvate, or glucose, based on wavelength-specific absorbance characteristics in the near-infrared spectrum;

a processor configured to:

receive said at least one near infrared measurement from said at least one probe;

compare said at least one near infrared measurement with a predetermined threshold value for at least one predetermined compound;

determine said at least one near infrared measurement is above said predetermined threshold value;

generate an indication indicating the presence of a secondary brain insult in the brain tissue; and, provide the indication to an output, thereby notifying an operator of said at least one probe of the presence of the secondary brain insult in the brain tissue, wherein the indication is generated based on bio-chemical identification of the excitotoxic compound;

wherein a first probe of said at least one probe is positioned adjacent to a primary insult and a second probe of said at least one probe is positioned adjacent to a medulla oblongata of a subject such that exci-totoxic compound concentrations measured at the two probe locations are compared to localize and identify progression of secondary brain insult.

2. The system according to claim 1, wherein said at least one probe includes at least one camera operative to provide visual feedback of the location of said at least one probe within the brain tissue.

3. The system according to claim 1, wherein the output includes a display operative to display the indication as a color.

4. The system according to claim 1, wherein said at least one probe comprises:

an emitter configured to emit near infrared light in a direction of the brain tissue;

a detector configured to detect a reflected light from the brain tissue and provide said at least one near infrared measurement of the reflected light.

5. The system according to claim 1, wherein said at least one probe comprises:

a first fiber bundle configured to direct the near infrared light from said emitter to the brain tissue; and, a second fiber bundle configured to direct the reflected light from the brain tissue to said detector.

6. The system according to claim 1, further comprising a memory unit configured to:

store said predetermined threshold value;

store at least one near infrared measurement; and, store a location where the secondary brain insult is detected.

7. The system according to claim 1, wherein the processor is configured to operate said at least one probe to obtain said at least one infrared measurement.

8. The system according to claim 1, wherein said prede-termined compound is Glutamate.

9. The system according to claim 1, wherein said prede-termined compound is Glucose.

10. The system according to claim 1, wherein said pre-determined compound is Lactate.

11. The system according to claim 1, wherein said pre-determined compound is Pyruvate.

* * * * *